(12) United States Patent
Colantonio et al.

(10) Patent No.: US 8,828,327 B2
(45) Date of Patent: *Sep. 9, 2014

(54) APPARATUS FOR STERILIZING A TUBULAR MEDICAL LINE PORT

(75) Inventors: Anthony J. Colantonio, Meadville, PA (US); Menno D. Jager, Meadville, PA (US)

(73) Assignee: PSI Medical Catheter Care, LLC, Erie, PA (US)

( * ) Notice: Subject to any disclaimer, the term of this patent is extended or adjusted under 35 U.S.C. 154(b) by 182 days.

This patent is subject to a terminal disclaimer.

(21) Appl. No.: 12/806,846

(22) Filed: Aug. 23, 2010

(65) Prior Publication Data
US 2012/0042466 A1 Feb. 23, 2012

(51) Int. Cl.
*A61L 2/00* (2006.01)
*A61M 39/20* (2006.01)
*A46B 15/00* (2006.01)
*A46B 9/02* (2006.01)

(52) U.S. Cl.
CPC ............... *A46B 9/02* (2013.01); *A46B 15/0055* (2013.01); *A46B 2200/3013* (2013.01); *Y10S 604/905* (2013.01)

USPC .......................................... 422/294; 604/905

(58) Field of Classification Search
USPC ........................................ 422/294; 604/905
See application file for complete search history.

(56) References Cited

U.S. PATENT DOCUMENTS

| 5,514,098 | A | * | 5/1996 | Pfoslgraf et al. | .......... | 604/167.04 |
| 2008/0235888 | A1 | * | 10/2008 | Vaillancourt et al. | ...... | 15/104.94 |
| 2010/0172794 | A1 | * | 7/2010 | Ferlic et al. | ..................... | 422/28 |

\* cited by examiner

*Primary Examiner* — Kevin Joyner
(74) *Attorney, Agent, or Firm* — Carothers and Carothers

(57) ABSTRACT

A scrubbing cap for sterilizing a tubular medical line port wherein the cap is molded of a pliable plastic and is provided with an open annular cavity therein which is dimensioned and contoured to receive through its mouth a tubular medical line port with a friction fit for scrubbing surfaces of the port with sterilizing liquid contained in the cavity. Flexible scrubber protrusions coaxially extend into the cavity from the floor of the cavity for scrubbing interior portions of the medical line port. The floor is flexibly displaceable whereby the floor will displace or bulge outwardly when the scrubber protrusions engage a valve within the port for thereby scrubbing the exposed surfaces of the valve while preventing inadvertent opening of the valve.

8 Claims, 2 Drawing Sheets

APPARATUS FOR STERILIZING A TUBULAR MEDICAL LINE PORT

FIELD OF THE INVENTION

The present invention relates to the field of medical liquid administration, and more particularly, to an apparatus and method for applying antiseptic to the female end of a medical infusion apparatus.

BACKGROUND OF THE INVENTION

Improvements in patient safety have been among the primary concerns of many efforts in today's healthcare industry. Healthcare associated infections remain a major area of focus for these efforts. The Center for Disease Control and Prevention cites healthcare associated infections in the top ten leading causes of death in the United States. Annually, healthcare associated infections account for an estimated 1.7 million infections in hospitals, 99,000 associated deaths, and 4.5 to 5.7 billion dollars in added patient care costs.

The reduction of healthcare associated infections depends upon awareness and adherence to aseptic technique when handling medical equipment that comes into direct contact with a patient. Medical equipment is constantly threatened by exposure to surrounding contaminated surfaces. These surfaces contain microorganisms (bacteria) which can easily adhere to the surface of medical equipment. Once contaminated, the medical equipment becomes a danger to the patient and can serve as a silent killer.

Healthcare institutions use millions of intravenous catheters each year. These catheters are at risk of contamination by a variety of mechanisms. One such mechanism relates to the contamination of the exposed ports of intravenous administration sets. This particular problem arises when an intravenous infusion line is temporarily disconnected from a patient (a process which can occur multiple times per day for an individual patient). During the time that the infusion line is disconnected from the patient, the exposed port of the intravenous line may contact potential contaminants. These contaminants could then lead to infection within a patient's bloodstream.

The critical event in the aforementioned circumstance is the failuer to retain the sterility of the intravenous port(s) and failuer to adequately disinfect the port in the instance of inadvertent contamination during the time of disconnect from infusion tubing. This risk is, in part, an unanticipated outcome of the somewhat recent implementation of needleless intravenous systems.

Currently, many practitioners are not actively considering the risk of contamination and are not taking steps to secure the sterility of exposed ports. When efforts are made to maintain the sterility of exposed ports, these efforts are both cumbersome (and therefore at times skipped over), or they fail due to technical shortcomings.

Safe practice recommendations include the use of aseptic technique when handling medical infusion lines. The current aseptic technique, as pertains specifically to intravenous catheters, includes sterilizing the exposed ports used for intermittent infusions with alcohol prep pads between uses. Disinfecting the surfaces of medical equipment with alcohol is a well accepted and established practice. Evidence exists supporting the use of a one minute alcohol exposure as an adequate disinfecting technique.

Current practice often utilizes alcohol cloth swabs to accomplish the task of disinfecting the surface of medical equipment, including intravenous tubing ports. This method has faults limiting its use. The exposure of the port to the cloth swab of alcohol is often performed in variable fashion. With variable techniques and inadequate exposure times to the disinfectant, successful sterilization is unlikely over the entirety of the surface area on female ports and port valve surfaces. In addition, the current standard disinfecting system of using an alcohol pad exposes the port, to the skin of the practitioner during and immediately after the disinfecting process. Lastly, the alcohol prep pads containing the cloth swabs may not be immediately available for use at the time of greatest need.

The port protection system disclosed in this invention description includes a means to temporarily and safely cover and apply antiseptic to the female end and end internal surfaces of a medical infusion apparatus. In this way, the device and associated method described will adequately provide a means to maintain the sterility of an indwelling intravenous administration set (or other medical infusion line), including any exposed internal valve surface, that has been disconnected from a patient until it is ready to be reattached for future use.

Some tubular medical line ports are needleless access devices which include a valve mechanism. It is an object of the present invention to provide an apparatus for sterilizing such tubular medical line ports, including the exposed valve surfaces, without risking inadvertent activation or depression of the mechanical valve inside the device, as this would open up the IV tubing and fluid pathway towards the patient.

SUMMARY OF THE INVENTION

The apparatus of the present invention for sterilizing a tubular medical line port comprises a cap unitarily molded of a flexible and pliable plastic and having an open annular cavity therein which is dimensioned and contoured to receive through the mouth of the cavity a tubular medical line port with a friction fit for scrubbing surfaces of the port with sterilizing fluid that is contained in the cavity. Flexible scrubber protrusions coaxially extend into the cavity from the floor of the cavity for scrubbing interior portions of the medical line port. The floor of the cavity is flexibly displaceable whereby the floor will displace when scrubber protrusions engage a valve within the port for thereby scrubbing exposed surfaces of the valve while preventing opening of the valve.

Inwardly directed flexible or pliable sidewall protrusions are provided on the sidewalls of the cavity for scrubbing exterior surfaces or sidewalls of the port to be scrubbed and sterilized. The sidewall protrusions may be comprised of luer threads for threadably engaging the port.

An annular inwardly protruding ring of the pliable material is provided at the mouth of the cap for stretched engagement with the port to inhibit escape of sterilization liquid contained in the cavity. In addition, the internal side walls of the cavity may be roughened to increase liquid surface tension for more effective retention to the internal sidewalls of the sterilization liquid.

The floor of the cavity is provided with an inwardly convex cross section and is integrally molded with the remainder of the cap. The cross section of the floor is thinner than the sidewalls of the cap whereby the floor will flexibly budge outward upon application of predetermined forces applied to the scrubber protrusions by a valve mechanism within the tubular medical line port being scrubbed in order to thoroughly scrub the valve surfaces but prevent depression or actuation thereof. The scrubber protrusions are integrally molded of the flexible or pliable plastic with the cap and the scrubber protrusions are coaxially arranged bristles.

Bottom side walls of the cap extend below the floor and thereby provide a bottom cavity in the cap for receiving the floor therein when it is displaced. Accordingly, accidental engagement of the displaced floor from the exterior of the cap is alleviated in order to prevent accidental engagement and depression of the floor and unintentional opening of the valve.

The convex floor area of the cavity, the side walls of the cavity and threads therein, together with the scrubber protrusions protruding upwardly from the floor create in effect a reservoir wherein the alcohol is trapped therein because the physical design of this reservoir area causes the surface tension to be high. This allows the alcohol retention when the device is inverted.

BRIEF DESCRIPTION OF THE DRAWINGS

Other objects and advantages appear hereinafter in the following description and claims. The accompanying drawings show, for the purpose of exemplification, without limiting the scope of the invention or the appended claims, certain practical embodiments of the present invention wherein:

DETAILED DESCRIPTION OF THE PREFERRED EMBODIMENTS

Figure 1:
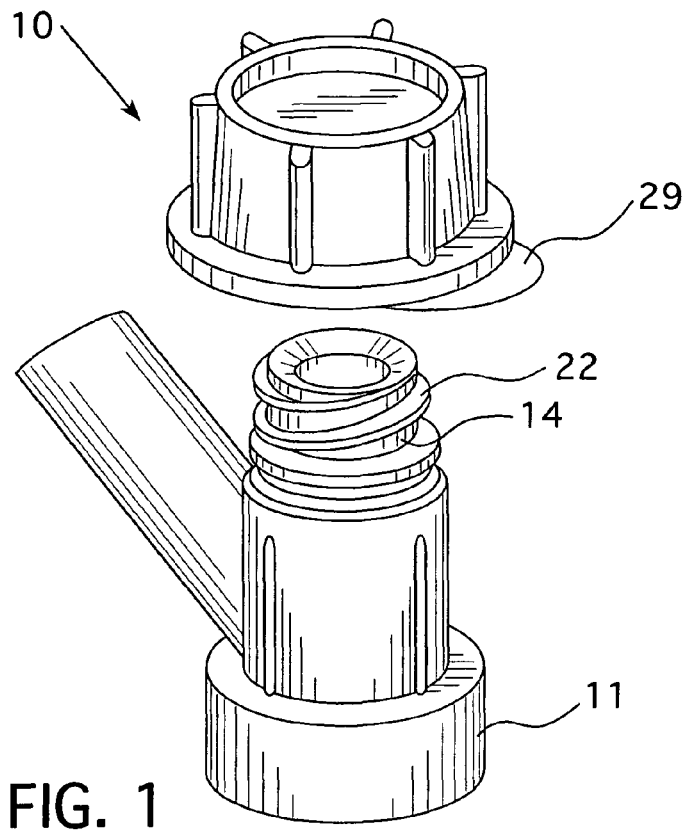
FIG. 1 is an exploded perspective view illustrating the sterilizing cap of the present invention just prior to engagement with a tubular medical line port to be sterilized.
Figure 2:
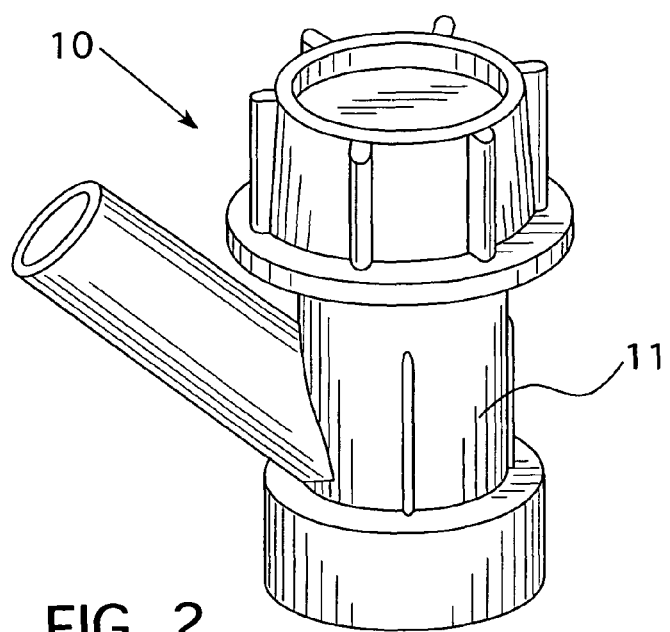
FIG. 2 is a perspective view of the combination shown in FIG. 1 after the sterilizing cap has been engaged with the tubular medical line port to be sterilized.

Referring to the drawings, the cap 10 of the present invention for sterilizing a tubular medical line port, such as the needleless access device 11, is integrally molded of a flexible and pliable plastic, such as a thermoplastic elastomer (TPE), and is provided with an open annular cavity 12 therein that is dimensioned and contoured to receive therein through mouth 13 the tubular medical line port 11 with a friction fit for scrubbing exterior surfaces 14 of the port 11 with a sterilizing fluid, such as alcohol, contained in the cavity 12. Flexible scrubber protrusions 15 coaxially extend into cavity 12 from the floor 16 of the cavity 12 for scrubbing interior portions 17 of medical line port 11.

Figure 4:
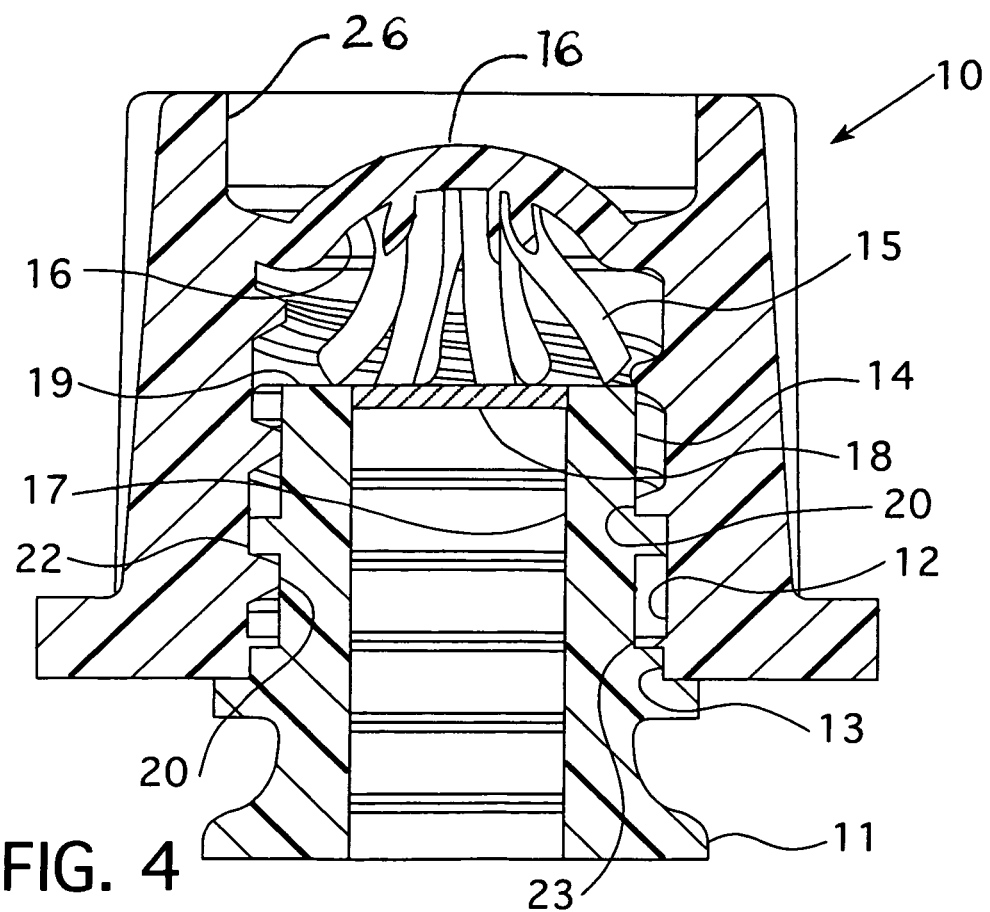
FIG. 4 is a view in vertical mid cross section of the sterilizing cap of the present invention in combination with a medical line port being sterilized, wherein the medical line port includes a valve.

However, in the example illustrated in FIG. 4, the port 11 is provided with a valve in the form of check valve 18 and the coaxially arranged bristles in the form of scrubbing protrusions 15 therefore cannot enter the interior of port 11 to access the internal sidewall 17. Accordingly, the scrubbing protrusions 15 engage the outer surfaces of the valve 18 and the outer annular end surface 19 of port 11 for scrubbing thereof. The internal workings of check valve 18 is not shown. There are a number of different spring biased valves on the market.

As is best illustrated in FIG. 4, floor 16 is flexibly displaceable whereby the floor will displace or bulge upwardly as illustrated in FIG. 4 when the scrubber protrusions 15 engage valve 18 within port 11 with a predetermined force. This provides excellent sterilization scrubbing of the exposed surfaces of the valve 18 and the end surface 19 of port 11 while at the same time preventing accidental opening of valve 18 by depression thereof.

Inwardly directed flexible or pliable sidewall protrusions 20 on the sidewalls of cavity 12 are provided for scrubbing exterior sidewalls 14 of the port 11. The sidewall protrusions 20 are provided in the form of luer threads for theadably engaging the threads 22 on port 11. The port 11 may thus be threadably engaged with cap 10 and due to the flexible or pliable nature of the cap and its integral threads 20, port 11 may be continuously rotated beyond initial threadable engagement as the pliable threads 20 will readily distort. This provides insured sterilization scrubbing of the exterior surfaces 14 of port 11. Typically the cap 10 is left on port 11 for approximately ten seconds after scrubbing to insure sterilization. Cap 10 may also be further rotated if additional scrubbing is desired. The cap 10 may also be left on for up to ninety six hours for protection of the port 11 between uses.

An inwardly protruding pliable ring 23 is provided at mouth 13 of cap 10 for stretched engagement with port 11 to inhibit escape of a sterilization liquid contained in cavity 12. Internal sidewalls 24 of cavity 12 are roughened to increase liquid surface tension for more effective retention of the sterilization liquid to the sidewalls.

Figure 3:
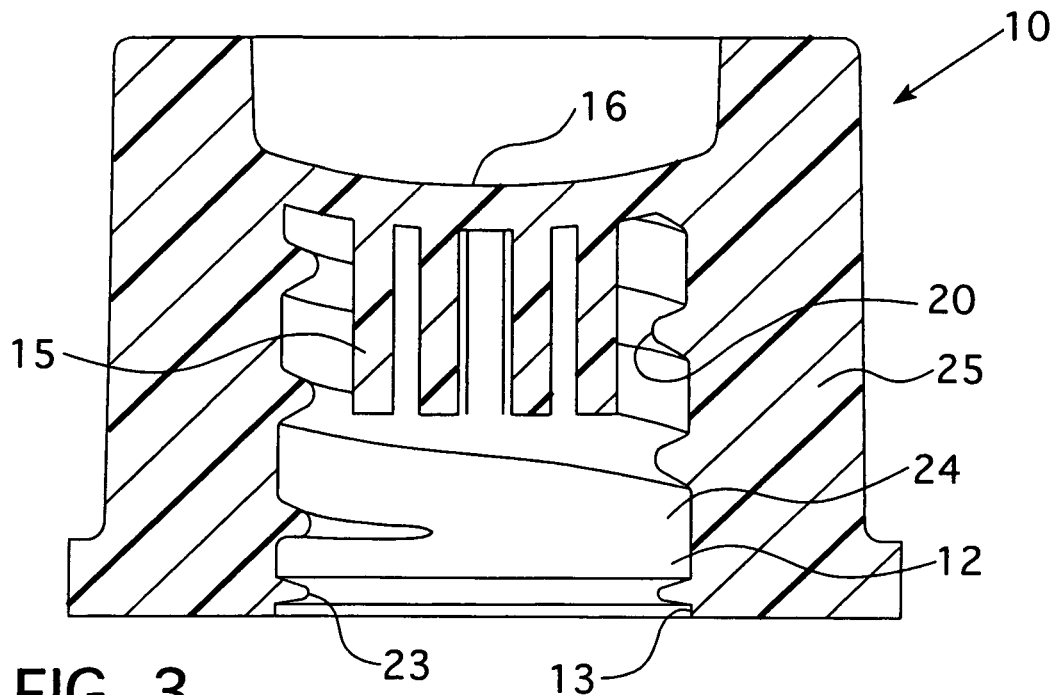
FIG. 3 is an enlarged view in vertical mid cross section of the scrubbing cap of the present invention.

Flexible floor 16 is provided with an inwardly convex cross section as best illustrated in FIG. 3 and is integrally molded with the remainder of cap 10. The cross section of floor 16 is thinner than the sidewalls 25 of cap 10 whereby floor 16 will flexibly bulge outward as illustrated in FIG. 4 upon application of predetermined forces applied to the scrubber protrusions 15 as illustrated in FIG. 4 when they are caused to pliably distort and forceably engage the outer annular surface 19 of port 11 and the outer surfaces of spring biased valve 18. Accordingly, accidental depression of the mechanical valve 18 is prevented while thorough and complete sterilization scrubbing of the outer surfaces of valve 18 is accomplished.

As is shown in FIG. 1, a peel-off seal 29 initially covers mouth 13 of cap 10 to prevent evaporation and loss of sterilization liquid contained in cavity 12.

The side walls 25 of cap 10 extend beyond or below floor 16 as indicated at 26 in FIG. 4. This accordingly provides a bottom cavity in cap 10 for receiving the floor 16 therein as illustrated in FIG. 4 when the floor 16 is displaced. The result is that accidental engagement of displaced floor 16 from the exterior of cap 10 is minimized and alleviated in order to prevent accidental opening of the valve 18 by accidental engagement and depression of the displaced floor 16. The space between convex floor 16, the internal walls of cavity 12, flexible scrubber protrusions 15 and internal threads 20 provide a reservoir for retaining disinfectant liquid, such as alcohol, whereby the alcohol is trapped between these surfaces because of the physical design which causes the surface tension to be highest in this region. This allows for alcohol retention when the device is inverted.

We claim:

1. Apparatus for sterilizing a tubular medical line port, comprising:
    an imperforate cap molded of a pliable plastic and having an open annular cavity with an integral floor and dimensioned and contoured to receive therein through a mouth a tubular medical line port with a friction fit for scrubbing surfaces of said port with a sterilizing fluid contained in said cavity;
    flexible scrubber protrusions extending into said cavity from a central portion of said floor of said cavity for scrubbing interior portions of a medical line port;
    said floor flexibly displaceable whereby said floor will displace outwardly when said scrubber protrusions engage a valve within said port for thereby scrubbing exposed surfaces of said valve while preventing opening of said valve:

said floor having an inwardly convex cross section such that said floor protrudes within said cavity and integrally molded with the remainder of said cap, said cross section being thinner than side walls of said cap whereby said floor will flexibly bulge outward upon application of predetermined forces applied to said scrubber protrusions;

said scrubber protrusions being integrally molded of said pliable plastic with said cap.

2. The apparatus of claim 1, inwardly directed pliable sidewall protrusions on sidewalls of said cavity for scrubbing exterior side walls of said port.

3. The apparatus of claim 2, wherein said sidewall protrusions are comprised of luer threads for threadably engaging said port.

4. The apparatus of claim 1, including a pliable and annular inwardly protruding ring at said mouth for stretched engagement with said port to inhibit escape of a sterilization liquid contained in said cavity.

5. The apparatus of claim 1, wherein internal sidewalls of said cavity are roughened to increase liquid surface tension for more effective retention thereto of sterilization liquid.

6. The apparatus of claim 1, wherein said scrubber protrusions are coaxially arranged bristles.

7. The apparatus of claim 1, including a peel-off seal covering said mouth.

8. The apparatus of claim 1, including bottom side walls of said cap extending below said floor and thereby providing a bottom cavity in said cap for receiving said floor therein when displaced whereby accidental engagement of said displaced floor from the exterior of said cap is alleviated in order to prevent opening of said valve.

* * * * *